United States Patent [19]

Mercer

[11] Patent Number: 4,537,775
[45] Date of Patent: Aug. 27, 1985

[54] THERAPEUTIC TREATMENT FOR VIRAL INFECTIONS

[76] Inventor: James B. Mercer, 13109 W. 95th St., Lenexa, Kans. 66215

[21] Appl. No.: 407,808

[22] Filed: Aug. 13, 1982

Related U.S. Application Data

[63] Continuation-in-part of Ser. No. 64,072, Aug. 6, 1979, Pat. No. 4,346,095.

[51] Int. Cl.³ ............................................. A61K 31/415
[52] U.S. Cl. ...................................... 514/398; 514/825
[58] Field of Search ..................................... 424/273 R Primary Examiner—Jerome D. Goldberg
Attorney, Agent, or Firm—Litman, Day and McMahon

[57] ABSTRACT

The administration internally to humans of 1-(B-hydroxethyl)-2-methyl-5-nitroimidazole, (metronidazole) in a dosage range for adult humans of about 31–2,500 mgs per twenty-four hour period, is an effective therapeutic treatment for certain viral infections causing diverse symptoms, both acute and chronic. Corresponding dosage proportional to body weight appears effective in other mammals also.

10 Claims, No Drawings

THERAPEUTIC TREATMENT FOR VIRAL INFECTIONS

This is a continuation-in-part of application Ser. No. 064,072 filed Aug. 6, 1979, entitled THERAPEUTIC TREATMENT FOR VIRAL INFECTIONS, now U.S. Pat. No. 4,346,095. Reference is made to related U.S. Pat. Nos. 4,073,928; 3,752,889; 3,856,966 and 3,952,103.

The invention herein described relates to a method of treating certain viral infections in humans, such as regional ileitis (Crohn's disease), viral thyroiditis, multiplesclerosis, viral hepatitis, carpal tunnel syndrome, psoriasis, amyotrophic lateral sclerosis, cytomegalovirus infection, viral bilateral macular degeneration of the retina, sarcoidosis, viral diverticulitis and measles (Rubeola). The treatment also appears to be effective against herpes simplex viral, herpes zoster viral; and infectious mononucleosis viral infections. Administration of the drug has also controlled certain of the so-called "dread diseases" including: atheroarteriosclerosis, rheumatoid arthritis and juvenile rheumatoid arthritis. The treatment also appears effective in the extension of life span which may result from the inhibition of such continuing viral disease. In other mammals, viral diseases such as distemper apparently respond to the treatment. It is noted that multiple sclerosis in humans has been linked to canine distemper virus in humans.

The objects of this invention are: to provide a method for systematically treating certain viral infections in humans; to provide such a treatment which is effective in combating viral infections in humans such as regional ileitis (Crohn's disease), viral thryoiditis, multiplesclerosis, viral hepatitis, carpal tunnel syndrome, psoriasis, amyotrophic lateral sclerosis, cytomegalovirus infection, viral bilateral macular degeneration of the retina, measles and corresponding diseases in other mammals such as distemper and scrapie in sheep; to provide such a method which appears effective in the suppression of herpes viral infections and other similar viral infections; to provide such a method which appears effective in the treatment of atheroarteriosclerosis, rheumatoid arthritis and juvenile rheumatoid arthritis; to provide such a method which appears effective in the extension of life span which may result from the inhibition of continuing viral disease; to provide such a method that is suitable for intensive therapy as well as long-term maintenance and intermittent therapy; and to provide such a treatment which is easily administered and usually well tolerated by the recipient.

1-($\beta$-hydroxyethyl)-2-methyl-5-nitroimidazole, (metronidazole) is a known alkylating agent of relatively low toxicity in mammals which is thought to interfere with nucleic acid biosynthesis. In the chemical name for metronidazole, $\beta$ is the greek letter beta and is a conventional abbreviation for stereochemistry. It appears that metronidazole can penetrate all tissues of the body quite readily and its effectiveness, in the treatment of viral infections, is believed to relate to blockage or interference with the viral metabolism cycle necessary for cell infection. The agent apparently suppresses viral production while natural body defenses function to eliminate viral material from the system. Metronidazole is readily absorbable from the human intestinal tract and may be administered orally as well as intraveneously or by vaginal or rectal inserts, as indicated.

Clinical observations upon the administration of metronidazole have demonstrated marked patient improvement and in many cases, apparent complete remissions in statistically significant numbers of patients diagnosed as suffering from regional ileitis (Crohn's disease), viral thyroiditis, multiple-sclerosis, viral hepatitis, viral diverticulitis, carpal tunnel syndrome, psoriasis, cytomegalovirus infection, viral macular degeneration of the retina, measles, herpes simplex and herpes zoster viral infections, as well as atheroarteriosclerosis, rheumatoid arthritis and juvenile rheumatoid arthritis. Where the viral infection was suspected in view of a broad general deterioration, but specific diagnosis was inconclusive, the treatment often appeared effective in combating the degenerative aging process, lengthening life and maintaining strength. In non-human mammals, the treatment is considered apparently effective in controlling such viral diseases as distemper and scrapie in sheep.

A typical intense treatment for an average size human adult patient comprises 500 mgs of the agent three to four times daily for a period of many months, then a reduction to 250 mgs three to four times daily for many additional weeks and thereafter further reduction or discontinuance, depending upon the tolerance of the patient and absence of symptoms. Doses for children and veterinary use are proportionally less according to body weight.

An alternative method of treatment is to give 1000 to 2500 mg. per day in a single dose on a daily basis for 6 days out of seven days. This method at higher dosage levels protects the patient from developing a peripheral neuropathy. The larger the single doses, the longer the time becomes between doses, i.e., five to ten grams of metronidazole may be given three times per week with safety from peripheral neuropathy.

As a more specific example of treating a child, an eight year old white female developed a rash on her arms and legs; her eyes were watery, and she complained of itching. She had not received a measles virus injection prior to the onset of the disease. When the patient was seen, she appeared to have contracted measles and exhibited a temperature of 102.8 degrees orally. She had a blotchy rash all over her body, with the characteristic measles cough. The patient was started on metronidazole, 125 mg t.i.d. with food and treated for one week. In less than twenty-four hours after starting treatment, there was a dramatic change in the child's subjective and physical signs; she was markedly improved with just a low grade temperature, 99.2 degrees orally, and the rash was rapidly fading. To confirm diagnosis, measles titers were taken two weeks apart, the first being less than one to eight; the latter being one to 32, which serilogically is diagnostic for measles.

It is suggested that consideration should be given to treating measles as noted rather than the use of live virus injection, which has been associated with the possibility of causing diseases such as multiple-sclerosis. Also, if a reliable early detection of multiple-sclerosis can be developed, arrest and possible cure may be available through the disclosed treatment.

Another specific example concerned a forty-one year old white male who experienced marked fatigue and weakness to the point that he was unable to work at his job as an elevator installer. He developed severe nausea and vomited for forty-eight hours. His urine became dark, and he suffered marked abdominal pain. Positive diagnosis was infectious hepatitis. The patient was started on metronidazole 125 mgs t.i.d. with food and treated for about five months. Positive results were noticed in about five days after initiating treatment. He returned to full time work after about thirty-five days, and there has been no recurrence for over five years.

An ultimate effective long-time maintenance dose was found to be as low as 31 mgs per day. The most common effective maintenance dose has been determined to be about 250 mgs per day for a substantial percentage of patients, with 500 mgs per day being indicated and well tolerated for other patients, depending on age, size, and physical condition. A reasonable maximum dosage for adult humans appears to be about 1,500 to 2,500 mgs per day that may be given in a single dose for one week, then renewed after a 48 hour respite. Renewal of treatment has been found to be effective upon a return of symptoms after treatment was discontinued.

Regarding side effects, some persons were found to experience nausea but it generally disappeared after a few weeks. In rare instances, there was a slight soreness of the mouth or a white tongue indicating need for dosage reduction. Some dizziness and dryness of the mouth and vagina were occasionally noted, and a few persons complined of a bad taste. Also, moderate leukopenia was occasionally observed, which normally returned to normal after dosage reduction, completion of a treatment regimen or as therapy continued.

Metronidazole is believed contraindicated in patients under treatment with desulfadram (Antabuse) and in hypothyroid patients. Because metronidazole appears to cross the placental barrier and enter the fetal circulation rapidly, and since its effects on fetal development are definitely known, it should be given during the first trimester of pregnancy if a viral infection has been suspected. Metronidazole, when given the first trimester or pregnancy, reduces the number of still births, major and minor fetal abnormalities. It appears the metronidazole should be given any time in pregnancy when the mother has a viral disease so as to prevent mental retardation and other fetal abnormalities caused by viral infections.

The initial neurological signs of metronidazole overdose in humans appear to be increased pulse rate, difficulty in reading small print, difficulty in handling small objects and insomnia. Progressively, it is understood that tachycardia may occur, and a slightly unstable person, especially, may suffer marked swings in mood. Physical exercise apparently becomes increasingly fatiguing, and weight loss occurs in spite of substantial food intake. When the medication is withdrawn, the adverse reaction usually clears in one week.

The metronidazole treatment described does not appear to damage the hematopoietic or the reticuloendothelial systems.

Over the past several years, metronidazole has been tried with various effectiveness for the treatment of trichomonas vaginalis infections, alcoholism, ameobic dysentary, ameobic liver abcess, leishmaniasis and giardia infestations, acute ulcerative gingivitis, long standing indolent ischemic ulcers found in peripheral vascular disease, scleroderma, schizaphrenia and in diabetic retinopathy, but apparently its effectiveness in viral infections has not been heretofore known.

Metronidazole apparently interferes directly with the synthesis of DNA viruses, in a similar manner that occurs with cytosine arabinoside. Metronidazole also apparently interferes with protein synthesis, as uric acid levels increase during therapy and may in some instances manifest itself in acute gout.

Metronidazole is found to be an anti-viral agent that does not damage the mammalian immune system and is known to be active against DNA and RNA viral infections. These viral diseases, when uncontrolled for long periods of time, cause death from the degenerative diseases of aging that lead to key organ failure and death.

It appears that viral diseases often form reservoirs of infection in the neural ganglions of the central and spinal nervous system, and from these sites or reservoirs, bombard key target organs by movement over neural pathways until death occurs from malignant transformation of the chromosomes in the affected target or key organ cells or until viral arteritis leads to key organ death by obstruction of the arterial blood flow. It appears that metronidazole is capable of sterilizing the mammalian nervous system by controlling the latent viral disease if given in sufficient dosage over a period of time. The degenerative diseases of aging are controllable by dosages of metronidazole, until immune system failure occurs after a markedly extended life span.

A frequent contributor to duodenal ulcers and gastric ulcers is herpes simplex virus type 1. Metronidazole has been determined to be useful in the rapid healing of duodenal and gastric ulcers, known as peptic ulcers.

Acute myocardial infarction can occur as a result of a viral blister occurring on the endothelium of a coronary artery, with a resultant thrombus formation. This thrombosis can be such as to block a coronary artery and cause myocardial infarction, or if small, will heal to form an atheroateriosclerotic plaque. Recurrent herpes simplex virus-type 1 blisters which heal will allow the atheroateriosclerotic plaque to become enlarged and slowly obstruct the distal segments of the affected coronary artery. The continuing viral disease appears as a responsible factor in producing worsening coronary circulation and heretofore, has been ameliorated by bypass coronary artery surgery. The use of intravenous metronidazole could stop the continuing virion bombardment against the affected coronary artery or the affected cardiac conduction system and thereby lessen early complications following myocardial infarction that caused the athero arteriosclerosis. The mechanism by which continuing viral infections cause death in humans and in animals is the continual virion bombardment of key target organs along neural pathways from foci of long standing viral infection in the neural ganglions of the nervous system. It appears that metronidazole has the ability to either control these viral foci of infection in neural ganglions, either by killing the virus or by causing it to be arrested until aging causes immune system failure.

What is claimed and desired to be secured by Letters Patent is:

1. A method for treating a human host having viral thyroiditis, said method comprising:
   (a) repeatedly orally administering anti-viral thyroiditis infection effective amounts of a pharmaceutical composition which contains, as an active ingredient, 1-($\beta$-hydroxyethyl)-2-methyl-5-nitroimidazole, to a human host in need of said treatment.

2. A method for treating a human host having viral multiple sclerosis, said method comprising:
   (a) repeatedly orally administering anti-multiple sclerosis infection effective amounts of a pharmaceutical composition which contains, as an active ingredient, 1-(β-hydroxyethyl)-2-methyl-5-nitroimidazole, to a human host in need of said treatment.

3. A method for treating a human host having virally induced carpal tunnel syndrome, said method comprising:
   (a) repeatedly orally administering anti-carpal tunnel syndrome effective amounts of a pharmaceutical composition which contains, as an active ingredient, 1-(beta-hydroxyethyl)-2-methyl-5-nitroimidazole, to a human host in need of said treatment.

4. A method for treating a human host having viral psoriasis, said method comprising:
   (a) repeatedly orally administering anti-viral psoriasis effective amounts of a pharmaceutical composition which contains, as an active ingredient, 1-(β-hydroxyethyl)-2-methyl-5-nitroimidazole, to a human host in need of said treatment.

5. A method for treating a human host having viral amyotrophic lateral sclerosis, said method comprising:
   (a) repeatedly orally administering anti-amyotrophic lateral sclerosis infection effective amounts of a pharmaceutical composition which contains, as an active ingredient, 1-(β-hydroxyethyl)-2-methyl-5-nitroimidazole, to a human host in need of said treatment.

6. A method for treating a human host having cytomegaloviris, said method comprising:
   (a) repeatedly orally administering anticytomegalovirus infection effective amounts of a pharmaceutical composition which contains, as an active ingredient, 1-(β-hydroxyethyl)-2-methyl-5-nitroimidazole, to a human host in need of said treatment.

7. A method for treating a human host having virally induced macular degeneration of the retina, said method comprising:
   (a) repeatedly orally administering anti-macular degeneration of the retina effective amounts of a pharmaceutical composition which contains, as an active ingredient, 1-(β-hydroxyethyl)-2-methyl-5-nitroimidazole, to a human host in need of said treatment.

8. A method for treating a human host having viral diverticulitis, said method comprising:
   (a) repeatedly orally administering anti-viral diverticulitis infection effective amounts of a pharmaceutical composition which contains, as an active ingredient, 1-(β-hydroxyethyl)-2-methyl-5-nitroimidazole, to a human host in need of said treatment.

9. A method for treating a human host having virally induced rheumatoid arthritis, said method comprising:
   (a) repeatedly orally administering anti-rheumatoid arthritis effective amounts of a pharmaceutical composition which contains, as an active ingredient, 1-(beta-hydroxyethyl)-2-methyl-5-nitroimidazole, to a human host in need of said treatment.

10. A method for treating a human host having virally induced juvenile rheumatoid arthritis, said method comprising:
   (a) repeatedly orally administering anti-juvenile rheumatoid arthritis effective amounts of a pharmaceutical composition which contains, as an active ingredient, 1-(beta-hydroxyethyl)-2-methyl-5-nitroimidazole, to a human host in need of said treatment.

* * * * *